(12) United States Patent
Sournac et al.

(10) Patent No.: US 9,561,114 B2
(45) Date of Patent: Feb. 7, 2017

(54) DISC-FACET VERTEBRAL DEVICE

(71) Applicant: MEDICREA INTERNATIONAL, Neyron (FR)

(72) Inventors: Denys Sournac, Reyrieux (FR); Thomas Mosnier, Anthon (FR)

(73) Assignee: MEDICREA INERNATIONAL, Neyron (FR)

( * ) Notice: Subject to any disclaimer, the term of this patent is extended or adjusted under 35 U.S.C. 154(b) by 387 days.

(21) Appl. No.: 14/344,832

(22) PCT Filed: Sep. 28, 2012

(86) PCT No.: PCT/IB2012/055191
§ 371 (c)(1),
(2) Date: Mar. 13, 2014

(87) PCT Pub. No.: WO2013/046169
PCT Pub. Date: Apr. 4, 2013

(65) Prior Publication Data
US 2014/0343679 A1    Nov. 20, 2014

(30) Foreign Application Priority Data

Sep. 30, 2011   (FR) ...................................... 11 58807

(51) Int. Cl.
*A61F 2/44*    (2006.01)
*A61F 2/30*    (2006.01)

(52) U.S. Cl.
CPC .......... *A61F 2/4425* (2013.01); *A61F 2/4405* (2013.01); *A61F 2002/30507* (2013.01); *A61F 2002/30517* (2013.01); *A61F 2002/30578* (2013.01); *A61F 2002/30665* (2013.01); *A61F 2002/448* (2013.01)

(58) Field of Classification Search
CPC ........ A61F 2/44; A61F 2/4405; A61F 2/4425; A61B 17/7064
USPC .............. 623/17.11, 17.16; 606/60, 246–249
See application file for complete search history.

(56) References Cited

U.S. PATENT DOCUMENTS

2005/0154461 A1*  7/2005  Humphreys .......... A61F 2/4405
                                                                    623/17.11
2009/0105757 A1    4/2009  Gimbel et al.

FOREIGN PATENT DOCUMENTS

WO       2005/067824       7/2005

OTHER PUBLICATIONS

International Search Report issued for corresponding International Patent Application No. PCT/IB2012/055191, mailed Dec. 13, 2012.

* cited by examiner

*Primary Examiner* — Si Ming Ku
(74) *Attorney, Agent, or Firm* — Myers Wolin, LLC

(57) ABSTRACT

A prosthesis includes: two pairs of elongated joint elements forming disc joint surfaces and facet joint surfaces; one pair of elements able to be positioned relative to each other. Each disc joint surface is in the shape of a hemisphere portion; positioning surfaces including posterior positioning surfaces; the prosthesis is associated with at least one rigid transverse element comprising positioning surfaces designed to be placed against the posterior positioning surfaces. Such placement permits one pair of joint elements to be positioned relative to the other pair of joint elements such that the disc joint surfaces are situated in a same geometric hemisphere.

10 Claims, 4 Drawing Sheets

DISC-FACET VERTEBRAL DEVICE

CROSS REFERENCE TO RELATED APPLICATIONS

The present disclosure is a national phase filing under 35 U.S.C. §371 of International Patent Application No. PCT/IB2012/055191, filed on Sep. 28, 2012, which claims priority to French Application No. 11 58807 filed on Sep. 30, 2011, the disclosures of each of which are expressly incorporated herein by reference in their entireties.

BACKGROUND OF THE INVENTION

The present invention relates to a total intervertebral joint prosthesis, i.e. a prosthesis for both the disc and facets.

The degeneration of an intervertebral disc is commonly treated by implanting an intervertebral disc prosthesis. Such a prosthesis nevertheless has the drawback of not treating the facet joints, which may also have deteriorated due to the repeated non-physiological movements of the vertebrae resulting from the degeneration of the disc.

Inappropriate implantation of an intervertebral disc prosthesis may also be a source of degeneration of the facet joints.

In order to resolve this problem, total vertebral joint prostheses have been designed, i.e. comprising prosthetic disc joint portions rigidly connected, by connecting arms, to prosthetic facet joint portions, cf. in particular patent application publication No. WO 2005/067824 A1. The disc joint and the facet joints are thus precisely positioned relative to one another, which allows precise control of the interactions of the disc joint with the facet joints.

Such a known combined prosthesis comprises two pairs of elongated elements designed for posterior implementation, one pair being designed to be placed in the intervertebral space on the left side of the vertebral bodies of the two considered vertebrae, and the other pair being designed to be placed in the intervertebral space on the right side of those vertebral bodies; each element of a pair of elements comprises a disc joint surface, a facet joint surface, and a connecting arm extending between said disc joint surface and said facet joint surface; when the two elements of a same pair of elements are placed one above the other, the disc joint surface of one element cooperates with the disc joint surface of the other element, and the facet joint surface of one element cooperates with the facet joint surface of the other element.

It nevertheless appears that the existing combined prostheses are not optimal. In fact, these prostheses can cause a risk of imperfect restoration of the physiological movement of the vertebrae, and, in particular, of being capable of undergoing significant wear over time. Certain prostheses include means for positioning one pair of elements relative to the other, which does not, however, exclude more or less significant imprecision in the positioning of one pair of elements relative to the other. Several other prostheses are purely and simply provided without means for positioning one pair of elements relative to the other. Furthermore, the existing combined prostheses have relatively complex and costly structures to manufacture.

OBJECTS OF THE INVENTION

The present invention aims to resolve these various drawbacks.

SUMMARY OF THE INVENTION

In a known manner, the prosthesis according to the invention comprises:
two pairs of elongated joint elements designed to be placed one above the other, one element of a pair of joint elements comprising a rounded disc joint surface, a facet joint surface, and a connecting arm extending between that disc joint surface and facet joint surface, and the other element of that pair of joint elements comprising a rounded disc joint surface, a facet joint surface, and a connecting arm extending between that disc joint surface and facet joint surface; when the two elements of a same pair are placed one above the other, the rounded disc joint surface of one element cooperates with the rounded disc joint surface of the other element, and the facet joint surfaces of the two elements cooperate with one another;
means for positioning one pair of elements relative to the other.

According to the invention,
each disc joint surface is in the shape of a hemisphere portion, that hemisphere having a same radius from one pair of joint elements to the next;
said positioning means comprise at least one first posterior positioning surface arranged on at least one element of a first pair of joint elements and at least one second posterior positioning surface arranged on at least one element of the second pair of joint elements;
the prosthesis is associated with at least one rigid transverse element that is capable to be connected to said first posterior positioning surface and said second posterior positioning surface, this rigid transverse element comprising at least one third positioning surface designed to be placed against said first posterior positioning surface and at least one fourth positioning surface designed to be placed against said second posterior positioning surface, this placement of said third and fourth positioning surfaces against said first and second positioning surfaces, respectively, making it possible to perform relative positioning of one pair of joint elements relative to the other pair of joint elements such that the disc joint surfaces of the joint elements are situated in a same geometric hemisphere.

It has in fact been possible to determine that the risk of imperfect restoration of the physiological movement of the vertebrae and wear over time of the existing total prostheses, using posterior introduction, resulted from the lack of creation of a precise central disc joint point, or imprecise positioning of one pair of joint elements relative to the other. This lack of precise central disc joint point is the source of defective operation of the disc joint and, consequently, the facet joints.

According to the invention, consequently, are provided:
disc joint surfaces in the form of a hemisphere portion,
first and second posterior positioning surfaces, at least one surface per pair of joint elements, and
an association of the prosthesis with a rigid transverse element equipped with third and fourth positioning surfaces, the arrival of the respective positioning surfaces of the joint elements and of the rigid transverse element achieving the positioning of the disc joint surfaces in a same geometric hemisphere.

It will be understood that "posterior" refers to the side of said joint elements located on the posterior side of the vertebral bodies after implantation.

As a result of this positioning, the disc joint surfaces jointly form a single joint ball for the upper joint elements relative to the lower joint elements, which allows a precise central disc joint point. This results in completely matched operation between the disc joint and the facet joint, and reduced wear of the disc and facet joint surfaces. Furthermore, the prosthesis according to the invention has a relatively simple and inexpensive structure to manufacture.

According to one embodiment of the invention, said rigid transverse element is made up of at least one crosspiece designed to be implanted with the prosthesis, by being fastened to said pairs of joint elements by fastening means.

According to another embodiment of the invention, said rigid transverse element is made up of at least one transverse strip comprised by an instrument for placing the prosthesis, this instrument being removed once said pairs of joint elements are positioned.

In both cases, said first and second posterior positioning surfaces and said third and fourth posterior surfaces may comprise means for positioning those surfaces against one another.

According to one simple embodiment of the invention, when said rigid transverse element is formed by said crosspiece, said positioning means are formed by holes arranged through the respective positioning surfaces, and by screws engaged through the corresponding pairs of holes, the screws also making up the means for fastening the crosspiece(s) to the corresponding joint elements.

According to one simple embodiment of the invention, when said rigid transverse element is made up of said strip, these positioning means are formed by holes arranged through the respective first and second posterior positioning surfaces and by lugs secured to said strip, capable of being engaged in said holes in an adjusted manner.

Advantageously,
said first and second posterior positioning surfaces are made up of lugs secured to the corresponding joint elements, these lugs being oriented and sized so as to extend across from pedicles of the vertebrae when said pairs of joint elements are placed between the bodies of the vertebrae to be treated, and comprising holes located across from those pedicles in that same position of said pairs of joint elements; and the prosthesis comprises anchor screws for anchoring the joint elements to the pedicles of the vertebrae, designed to be engaged in those holes, then in those pedicles.

The joint elements of the prosthesis are thus anchored to the pedicles of the vertebrae.

According to the preferred embodiment of the prosthesis according to the invention,
the two upper joint elements comprising lugs as previously cited protruding toward the upper side of those elements, said lugs being oriented and sized so as to be across from the pedicles of the underlying vertebra when the pairs of joint elements are in place on the vertebrae to be treated;
the two lower joint elements comprising lugs as previously cited protruding toward the lower side of those elements, said lugs being oriented and sized so as to be located across from the pedicles of the underlying vertebra when the pairs of joint elements are in place on the vertebrae to be treated;
two crosspieces as previously cited are associated with the prosthesis, one of which is designed to be connected to the two lugs of the upper joint elements and the other of which is designed to be connected to the two lugs of lower joint elements;

said lugs all comprise holes as previously cited and said crosspieces comprise holes coinciding with those holes comprised by the lugs; and
the prosthesis comprises anchor screws for anchoring the joint elements to the pedicles of the vertebrae, designed to be engaged in those holes, and in the pedicles.

The invention will be well understood, and other features and advantages thereof will appear, in reference to the appended diagrammatic drawing, showing, as non-limiting examples, two possible embodiments of the concerned prosthesis and rigid transverse elements associated with that prosthesis.

DESCRIPTION OF THE PREFERRED EMBODIMENTS

Figure 1:
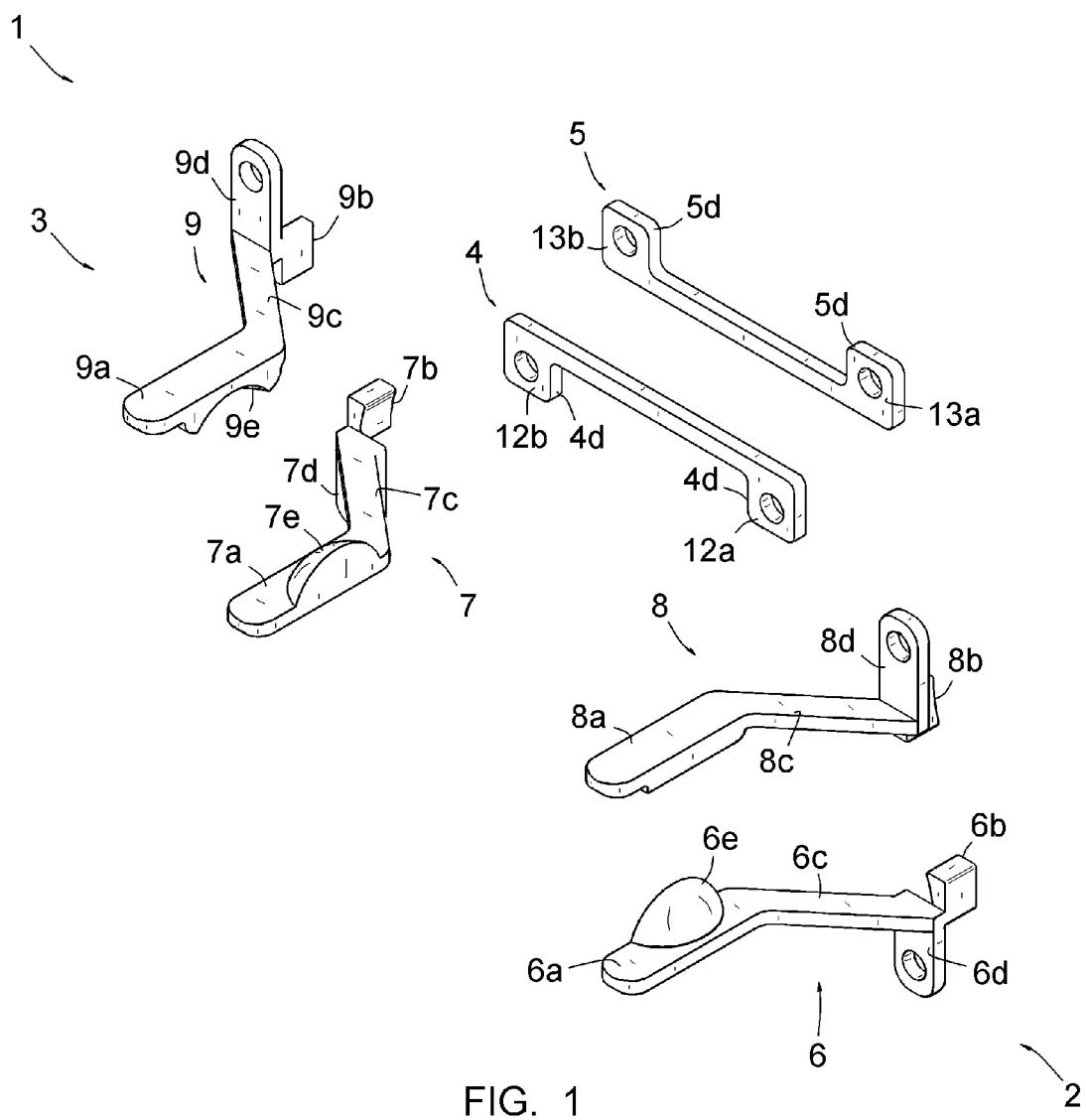
FIG. 1 is a perspective view of various elements comprised by the prosthesis and two rigid transverse elements according to the first embodiment.
Figure 2:
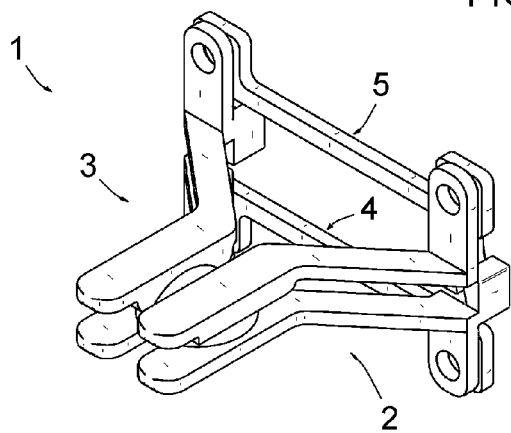
FIG. 2 is a perspective view similar to FIG. 1 of the elements shown by FIG. 1, in the assembled state of those elements.

FIGS. 1 to 4 show a combined disc-facet vertebral prosthesis 1, comprising two pairs 2, 3 of elongated joint elements 6 to 9. The prosthesis 1 also comprises screws (not shown) for anchoring the joint elements 6 to 9 to the pedicles of the vertebrae.

FIGS. 1 to 4 also show two crosspieces 4, 5 forming rigid transverse elements for positioning said pairs 2, 3 of joint elements 6 to 9 relative to the vertebrae to be treated.

As shown in FIGS. 5 to 8, the pair 2 of elements is designed for posterior insertion into the intervertebral space of the two vertebrae 100 to be treated and is designed to be placed on the left of the vertebral bodies of those vertebrae 100; the other pair 3 of elements is also designed for posterior insertion into said intervertebral space and is designed to be placed on the right of said vertebral bodies.

Each pair of elements 2, 3 comprises a lower joint element 6, 7 and an upper joint element 8, 9, and each joint element 6 to 9 comprises a disc portion 6a to 9a, a facet portion 6b to 9b, a connecting arm 6c to 9c, extending between the disc portion 6a to 9a and the facet portion 6b to 9b, and protruding lugs 6d to 9d.

The disc portions 6a to 9a comprise disc joint surfaces 6e to 9e in the form of a hemisphere portion, these hemispheres having a same radius from one pair of joint elements to the next. The lower disc joint surfaces 6e and 7e have a convex shape, and the upper disc surfaces 8e and 9e have a concave shape. The concave surfaces 8e and 9e of the pair of upper elements 8, 9 cooperate with the convex surfaces 6e and 7e of the pair of lower elements 6, 7 when said upper joint elements 8 and 9 are placed above the lower joint elements 6 and 7.

The facet portions 6b to 9b form facet joint surfaces. The joint surfaces 6b and 8b cooperate with one another to form a first prosthetic facet joint, and the joint surfaces 7b and 9b cooperate with one another to form a second prosthetic facet joint.

The connecting arms 6c to 9c have lengths such that the prosthetic facet joints are positioned, relative to the disc joint, in a manner close to the original anatomy.

The protruding lugs 6d to 9d are, as shown in FIGS. 5 to 8, oriented and sized so that their free end positions extend across from the pedicles 101 of the vertebrae 100 when the pairs 2, 3 of elements are placed between the bodies of those vertebrae. The lugs 6d, 7d of the two lower joint elements 6, 7 therefore protrude toward the lower side of those elements, toward the pedicles 101 of the underlying vertebra 100, and the lugs 8d, 9d of the two upper joint elements 8, 9 protrude toward the upper side of those joint elements 8, 9, toward the pedicles 101 of the underlying vertebra 100.

Figure 3:
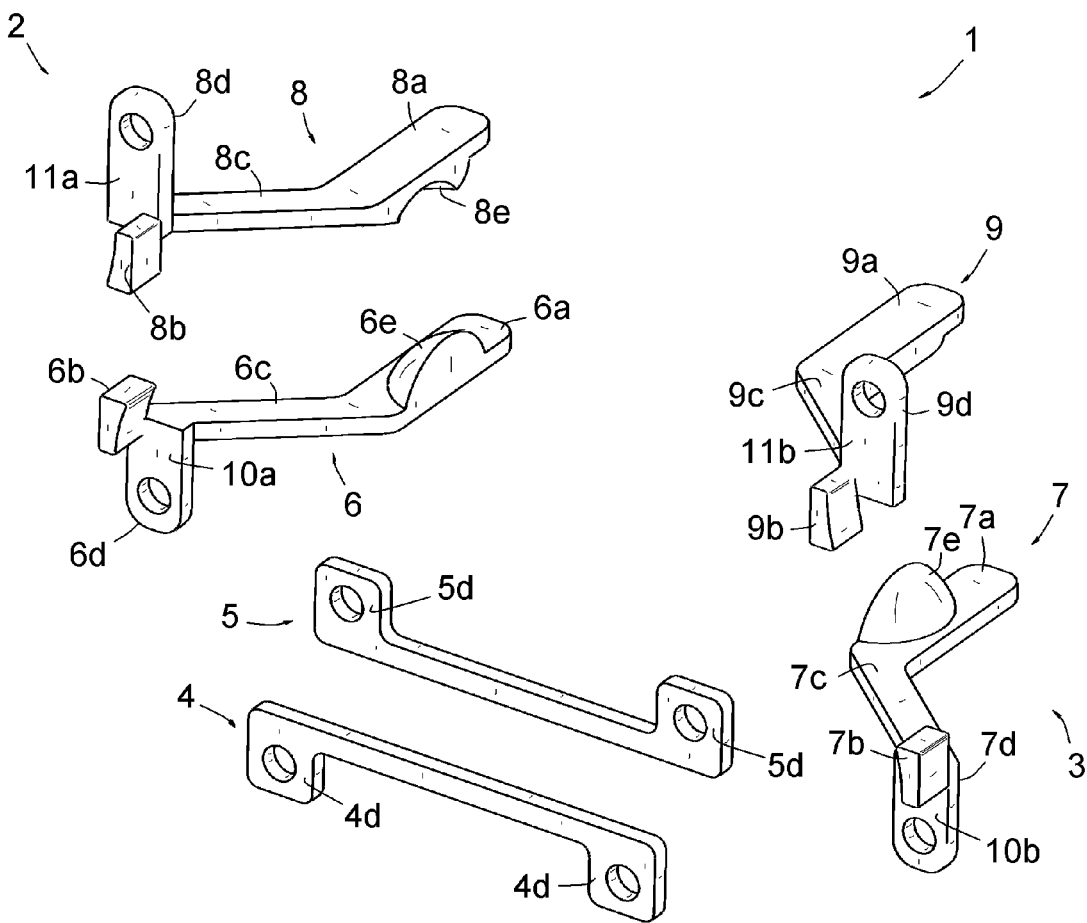
FIGS. 3 and 4 are perspective views of said elements from another angle, respectively similar to FIGS. 1 and 2.
Figure 4:
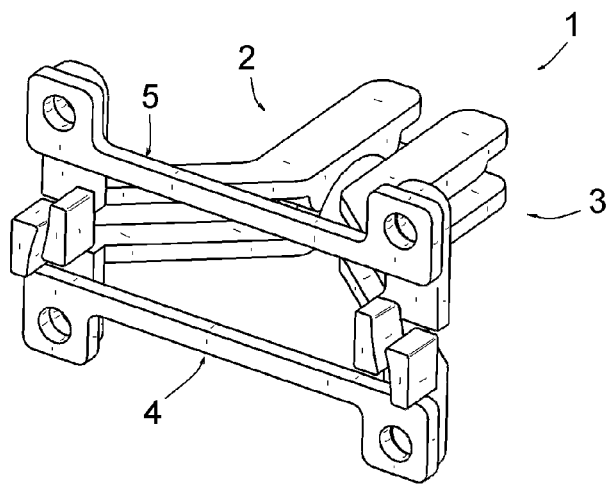
Figure 5:
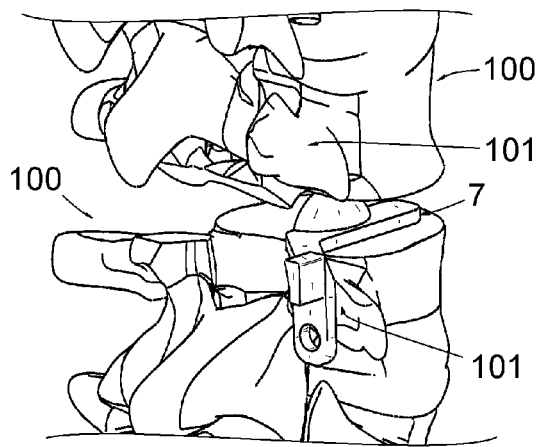
FIGS. 5 to 8 are perspective views of said elements during placement thereof on two vertebrae to be treated.
Figure 6:
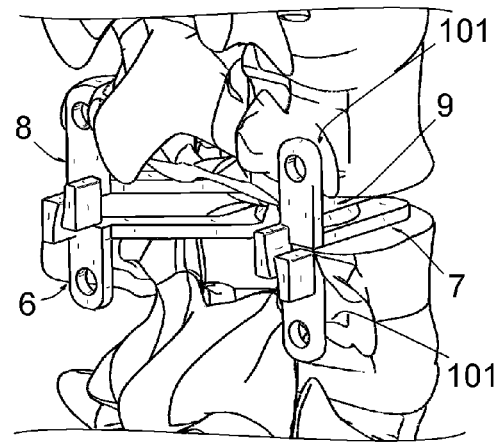
Figure 7:
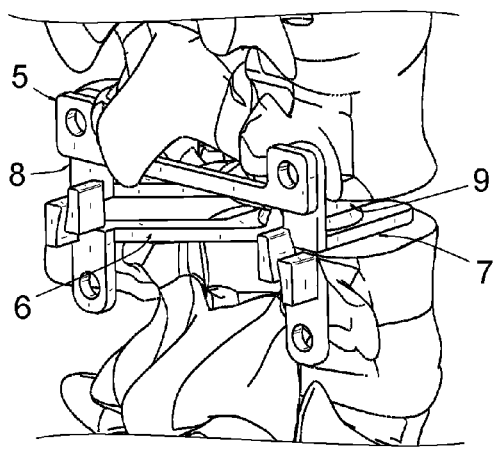
Figure 8:
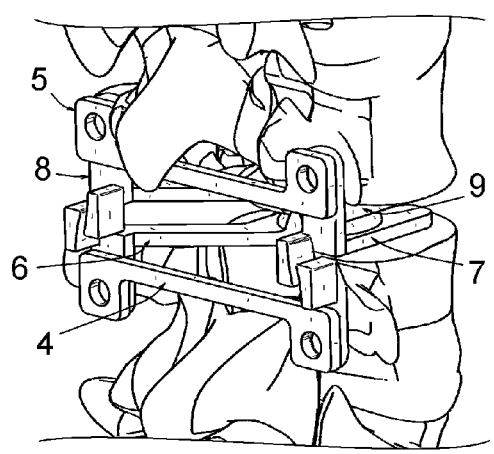

As particularly shown in FIG. 3, the base portions of the lugs 6d and 7d are flat and form first posterior positioning surfaces 10a, 10b, and the base portions of the lugs 8d and 9d are also flat and form two posterior positioning surfaces 11a, 11b. The free end portions of the lugs 6d to 9d comprise holes located across from the pedicles 101 when the pairs of elements 2, 3 are placed between the vertebrae 100.

The crosspieces 4, 5 each comprise two end lugs 4d, 5d. As particularly shown in FIG. 1, the lugs 4d of the crosspiece 4 form third coplanar flat positioning surfaces 12a, 12b, and the lugs 5d of the crosspiece 5 form fourth flat positioning surfaces 13a, 13b, which are also coplanar. Each lug 4d, 5d is pierced with a hole.

Figure 9:
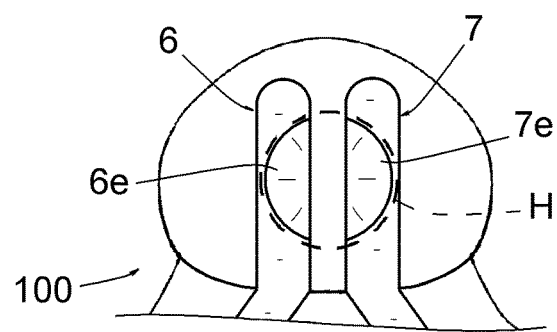
FIG. 9 is an apico-caudal view of the underlying vertebra and two joint elements placed on that vertebra.
Figure 10:
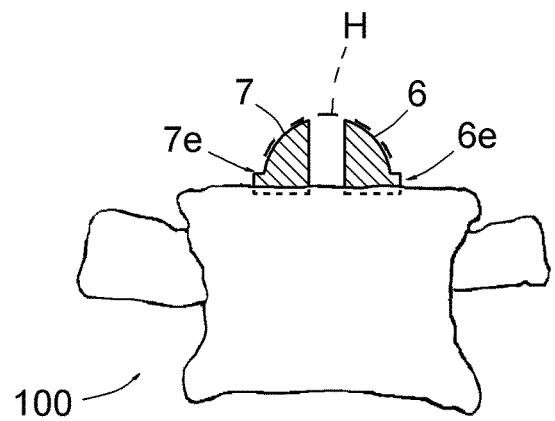
FIG. 10 is a front view of that underlying vertebra and those two joint elements.

As will be understood in reference to FIGS. 1 to 4, 7 and 8, the surfaces 12a and 12b of the lugs 4d are designed to be placed against the surfaces 10a and 10b of the two lugs 6d and 7d, in planar contact therewith, and the surfaces 13a and 13b of the lugs 5d are designed to be placed against the surfaces 11a and 11b of the upper joint elements 8 and 9, also in planar contact therewith; in this position, also shown in FIGS. 9 and 10, which corresponds to the implantation position of the pairs 2, 3 of joint elements, the disc joint surfaces 6e and 8e and the disc joint surfaces 7e and 9e are placed in a same geometric hemisphere H, both in a plane perpendicular to the apico-caudal axis (cf. FIG. 9) and in a frontal plane (cf. FIG. 10).

In practice, as shown in FIGS. 5 to 8, the joint elements 6 to 9 are successively placed between the vertebrae 100 to be treated (cf. FIGS. 5 and 6), through the posterior route, then the crosspieces 4 and 5 are positioned, with the lugs 4d, 5d placed against the lugs 6d to 9d (cf. FIGS. 7 and 8); the pairs 2, 3 of elements are then moved, if necessary, so as to bring the surfaces 10a to 11b formed by the lugs 6d to 9d into planar contact with the surfaces 12a to 13b formed by said lugs 4d, 5d.

Figure 11:
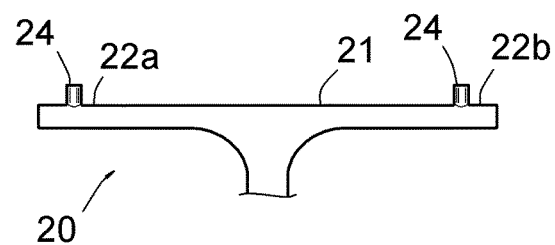
FIG. 11 is a partial view of a rigid transverse element according to the second embodiment.

This position correction of the pairs 2, 3 of elements may also be done, before positioning of the crosspieces 4, 5, using an instrument 20 as shown in FIG. 11. This instrument 20 comprises a transverse strip 21 that forms coplanar positioning surfaces 22a, 22b, homologous with the surfaces 12a, 12b or 13a, 13b, and lugs 24 capable of being engaged in an adjusted manner in the holes of the lugs 6d to 9d.

When the appropriate relative positions of the elements 6 to 9 are obtained, the instrument 20 is removed and crosspieces 4, 5 are positioned such that the holes of the lugs 4d, 5d coincide with the holes of the lugs 6d to 9d, then the aforementioned pedicle screws are placed through those respective holes and are inserted into the pedicles 101 to fasten the joint elements 6 to 9 to the vertebrae 100.

As a result of this positioning of the pairs 2, 3 of joint elements, the disc joint surfaces 6e to 9e jointly form a single joint ball for the upper joint elements 8 and 9 relative to the lower joint elements 6 and 7. The single ball has a precise disc joint point, which results in perfect restoration of the anatomical movement of the vertebrae 100 and reduced wear of the disc and facet joint surfaces over time. Furthermore, the prosthesis 1 has a relatively simple and inexpensive structure to manufacture.

In the second embodiment of the invention, the prosthesis 1 does not have crosspieces 4, 5; the pairs 2, 3 of joint elements are positioned using the instrument 20, then the aforementioned pedicle screws are placed directly through the holes of the lugs 6d to 9d.

The invention has been described above in reference to the embodiments provided as examples. It is of course not limited to these embodiments, but on the contrary encompasses all other embodiments covered by the appended claims.

What is claimed is:

1. A total intervertebral joint prosthesis, comprising:
two pairs of elongated joint elements designed to be placed one above the other, one element of a pair of joint elements comprising a rounded disc joint surface, a facet joint surface, and a connecting arm extending between that disc joint surface and that facet joint surface, and the other element of that pair of joint elements comprising a rounded disc joint surface, a facet joint surface, and a connecting arm extending between that disc joint surface and that facet joint surface; when the two elements of a same pair are placed one above the other, the rounded disc joint surface of one element cooperates with the rounded disc joint surface of the other element, and the facet joint surfaces of the two elements cooperate with one another;
a first positioning means for positioning the one pair of elements relative to the other;
wherein:
each of the disc joint surfaces is in the shape of a hemisphere portion, that hemisphere having a same radius from one pair of joint elements to the next;
said first positioning means comprise at least one first posterior positioning surface arranged on at least one element of a first pair of joint elements and at least one second posterior positioning surface arranged on at least one element of the second pair of joint elements;
the prosthesis is associated with at least one rigid transverse element that is capable to be connected to said first posterior positioning surface and said second posterior positioning surface, this at least one rigid transverse element comprising a third positioning surface designed to be placed against said first posterior positioning surface and a fourth positioning surface designed to be placed against said second posterior positioning surface, this placement of said third positioning surface and said fourth positioning surface against said first positioning surface and said second positioning surface, respectively, making it possible to perform relative positioning of one pair of joint elements relative to the other pair of joint elements such that the disc joint surfaces of the joint elements are situated in a same geometric hemisphere; and
said at least one rigid transverse element is made up of at least one crosspiece designed to be implanted with the prosthesis, by being fastened to said pairs of joint elements by fastening means.

2. The prosthesis according to claim 1, wherein said first posterior positioning surface and said second posterior positioning surface and said third positioning surface and said fourth positioning surface comprise a second positioning means for positioning those surfaces against one another.

3. The prosthesis according to claim 2, wherein said second positioning means are formed by holes arranged through the respective positioning surfaces, and by screws engaged through the corresponding pairs of holes, the screws also making up the means for fastening a crosspiece or crosspieces to the corresponding joint elements.

4. The prosthesis according to claim 2, wherein said second positioning means are formed by holes arranged through the respective first posterior positioning surface and the second posterior positioning surface and by lugs secured to a strip, capable of being engaged in said holes in an adjusted manner.

5. The prosthesis according to claim 1, wherein:
said first posterior positioning surface and said second posterior positioning surface are made up of lugs secured to the corresponding joint elements, these lugs being oriented and sized so as to extend across from pedicles of a vertebrae when said pairs of joint elements are placed between the bodies of the vertebrae to be treated, and comprising holes located across from those pedicles in that same position of said pairs of joint elements; and
the prosthesis comprises anchor screws for anchoring the joint elements to the pedicles of the vertebrae, designed to be engaged in those holes, then in those pedicles.

6. A total intervertebral joint prosthesis, comprising:
two pairs of elongated joint elements designed to be placed one above the other, one element of a pair of joint elements comprising a rounded disc joint surface, a facet joint surface, and a connecting arm extending between that disc joint surface and facet joint surface, and the other element of that pair of joint elements comprising a rounded disc joint surface, a facet joint surface, and a connecting arm extending between that disc joint surface and facet joint surface, and when the two elements of a same pair are placed one above the other, the rounded disc joint surface of one element cooperates with the rounded disc joint surface of the other element, and the facet joint surfaces of the two elements cooperate with one another; and
a positioning means for positioning the one pair of elements relative to the other;
wherein:
each of the disc joint surfaces is in the shape of a hemisphere portion, that hemisphere having a same radius from one pair of joint elements to the next,
said positioning means comprise at least one first posterior positioning surface arranged on at least one element of a first pair of joint elements and at least one second posterior positioning surface arranged on at least one element of the second pair of joint elements,
the prosthesis is associated with at least one rigid transverse element that is capable to be connected to said first posterior positioning surface and said second posterior positioning surface, this rigid transverse element comprising a third positioning surface designed to be placed against said first posterior positioning surface and a fourth positioning surface designed to be placed against said second posterior positioning surface, this placement of said third positioning surface and said fourth positioning surface against said first positioning surface and said second positioning surface, respectively, making it possible to perform relative positioning of one pair of joint elements relative to the other pair of joint elements such that the disc joint surfaces of the joint elements are situated in a same geometric hemisphere, and
wherein:
said at least one rigid transverse element is made up of at least one crosspiece designed to be implanted with the prosthesis, by being fastened to said pairs of joint elements by fastening means,
said first posterior positioning surface and said second posterior positioning surface are made up of lugs secured to the corresponding joint elements, these lugs being oriented and sized so as to extend across from pedicles of a vertebrae when said pairs of joint elements are placed between the bodies of the vertebrae to be treated, and comprising holes located across from those pedicles in that same position of said pairs of joint elements, and
the prosthesis comprises anchor screws for anchoring the joint elements to the pedicles of the vertebrae, designed to be engaged in those holes, then in those pedicles,
the lugs which two upper joint elements comprises protrude toward upper side of those elements, said lugs being oriented and sized so as to be across from the pedicles of upperlying vertebra when the pairs of joint elements are in place on the vertebrae to be treated;
the lugs which two lower joint elements comprises protrude toward the lower side of those elements, said lugs being oriented and sized so as to be located across from the pedicles of the upperlying vertebra when the pairs of joint elements are in place on the vertebrae to be treated;
the prosthesis includes two of said at least one crosspieces that are associated with the prosthesis, one of which is designed to be connected to the two lugs of the upper joint elements and the other of which is designed to be connected to the two lugs of lower joint elements; and
said holes which said lugs comprise and said crosspieces comprise holes capable to coincide with those holes comprised by the lugs.

7. A total intervertebral joint prosthesis, comprising:
two pairs of elongated joint elements designed to be placed one above the other, one element of a pair of joint elements comprising a rounded disc joint surface, a facet joint surface, and a connecting arm extending between that disc joint surface and that facet joint surface, and the other element of that pair of joint elements comprising a rounded disc joint surface, a facet joint surface, and a connecting arm extending between that disc joint surface and facet joint surface; when the two elements of a same pair are placed one above the other, the rounded disc joint surface of one element cooperates with the rounded disc joint surface of the other element, and the facet joint surfaces of the two elements cooperate with one another;
wherein:
each of the disc joint surfaces is in the shape of a hemisphere portion, that hemisphere having a same radius from one pair of joint elements to the next;
at least one first posterior positioning surface arranged on at least one element of a first pair of joint elements and at least one second posterior positioning surface arranged on at least one element of the second pair of joint elements are arranged to position the one pair of elements relative to the other;

the prosthesis is associated with at least one rigid transverse element that is capable to be connected to said first posterior positioning surface and said second posterior positioning surface, this at least one rigid transverse element comprising a third positioning surface designed to be placed against said first posterior positioning surface and a fourth positioning surface designed to be placed against said second posterior positioning surface, this placement of said third positioning surface and said fourth positioning surface against said first positioning surface and said second positioning surface, respectively, making it possible to perform relative positioning of one pair of joint elements relative to the other pair of joint elements such that the disc joint surfaces of the joint elements are situated in a same geometric hemisphere; and said at least one rigid transverse element is made up of at least one crosspiece designed to be implanted with the prosthesis, by being fastened to said pairs of joint elements by fasteners.

8. The prosthesis according to claim 7, wherein said first posterior positioning surface and said second posterior positioning surface and said third positioning surface and said fourth positioning surface comprise holes arranged through the respective positioning surfaces and screws engaged through the corresponding pairs of holes, the screws making up the fasteners of a crosspiece or crosspieces to the corresponding joint elements, to position those surfaces against one another.

9. The prosthesis according to claim 7, wherein said first posterior positioning surface and said second posterior positioning surface and said third positioning surface and said fourth positioning surface comprise holes arranged through the respective first posterior positioning surface and the second posterior positioning surface and lugs secured to a strip, capable of being engaged in said holes in an adjusted manner, to position those surfaces against one another.

10. The prosthesis according to claim 7, wherein:

said first posterior positioning surface and said second posterior positioning surface are made up of lugs secured to the corresponding joint elements, these lugs being oriented and sized so as to extend across from pedicles of a vertebrae when said pairs of joint elements are placed between the bodies of the vertebrae to be treated, and comprising holes located across from those pedicles in that same position of said pairs of joint elements; and the prosthesis comprises anchor screws for anchoring the joint elements to the pedicles of the vertebrae, designed to be engaged in those holes, then in those pedicles.

* * * * *